(12) United States Patent
Ziehler et al.

(10) Patent No.: US 9,044,329 B2
(45) Date of Patent: Jun. 2, 2015

(54) GARMENT WITH INTEGRAL SUPPORT SYSTEM

(76) Inventors: Thomas P. Ziehler, Clinton, OH (US);
Doreen M. Ziehler, Clinton, OH (US);
Margaret M. Ziehler, Uniontown, OH (US); William A. Ziehler, Saline, MI (US)

( * ) Notice: Subject to any disclaimer, the term of this patent is extended or adjusted under 35 U.S.C. 154(b) by 0 days.

(21) Appl. No.: 13/582,468

(22) PCT Filed: May 10, 2012

(86) PCT No.: PCT/US2012/037236
§ 371 (c)(1),
(2), (4) Date: Sep. 4, 2012

(87) PCT Pub. No.: WO2012/158442
PCT Pub. Date: Nov. 22, 2012

(65) Prior Publication Data
US 2014/0058312 A1    Feb. 27, 2014

Related U.S. Application Data

(60) Provisional application No. 61/485,791, filed on May 13, 2011.

(51) Int. Cl.
*A61F 13/00* (2006.01)
*A61F 5/40* (2006.01)
*A44B 9/02* (2006.01)

(52) U.S. Cl.
CPC .... *A61F 5/40* (2013.01); *A44B 9/02* (2013.01)

(58) Field of Classification Search
CPC ...... A61F 5/40; A63B 71/1216; A41B 9/001; A41B 9/002; A41B 9/004
USPC ........... 602/19, 24, 60–62, 68–73; 2/70, 227, 2/406, 408, 226, 466, 455, 456, 400–404, 2/407, 228; D2/712–713, 714–717
See application file for complete search history.

(56) References Cited

U.S. PATENT DOCUMENTS

| | | | | |
|---|---|---|---|---|
| 757,153 | A * | 4/1904 | Tainsh | 602/73 |
| 1,477,187 | A * | 12/1923 | Rayne | 602/71 |
| 1,592,732 | A * | 7/1926 | Friedman | 602/69 |
| 2,038,242 | A * | 4/1936 | Schwartz | 602/67 |
| 2,050,410 | A * | 8/1936 | Baer | 602/69 |
| 5,239,706 | A | 8/1993 | Stevenson | |
| 5,647,065 | A * | 7/1997 | Richerson | 2/403 |
| 6,041,441 | A * | 3/2000 | Counts et al. | 2/227 |
| 7,178,174 | B2 * | 2/2007 | Soderstrom | 2/403 |

(Continued)

*Primary Examiner* — Kim M Lewis
(74) *Attorney, Agent, or Firm* — Fraser Clemens Martin & Miller LLC; Williams A. Ziehler

(57) ABSTRACT

An article of apparel, including a garment such as underwear, boxers, or briefs is provided that has an integral support system. The garment is configured to provide improved genital support while the wearer exercises, plays sports, or engages in a physical activity. The garment includes a portion configured as an article of clothing such as underwear, for example, made of cotton and spandex/elastane material, and includes a support pouch, a wide waistband, support straps slidingly disposed through retaining means, and other supportive features. Use of the garment can eliminate the need for the user to wear multiple support layers or uncomfortable compression underwear in order to gain adequate support while exercising, playing sports, or engaging in other physical activities.

17 Claims, 4 Drawing Sheets

(56) References Cited

U.S. PATENT DOCUMENTS

| | | | |
|---|---|---|---|
| 7,296,307 B2 * | 11/2007 | Atwater et al. | 2/466 |
| 2004/0031088 A1 | 2/2004 | Soderstrom | |
| 2005/0204458 A1 | 9/2005 | Wong | |
| 2006/0211974 A1 * | 9/2006 | Bland et al. | 602/67 |
| 2010/0095433 A1 * | 4/2010 | Turkbas | 2/228 |

\* cited by examiner

GARMENT WITH INTEGRAL SUPPORT SYSTEM

CROSS-REFERENCE TO RELATED APPLICATIONS

This application is a U.S. National Stage of International Application No. PCT/US2012/037236 filed on May 10, 2012, which claims the benefit of U.S. Provisional Application No. 61/485,791, filed on May 13, 2011. The entire disclosures of the above applications are incorporated herein by reference.

FIELD

The present technology relates to garments providing an integral support system, including garments that can be worn during various physical or athletic activities.

INTRODUCTION

This section provides background information related to the present disclosure which is not necessarily prior art.

Particular supportive and protective undergarments are worn by various persons, such as males, during various physical and athletic activities and after certain medical procedures, such as hernias and vasectomies, to provide support and protection to the genitalia. For example, such undergarments include athletic supporters having an elongated knitted pouch attached to a wide waistband with leg straps that extend from the bottom of the pouch at the crotch around the legs attaching at the waistband at the backside of the wearer. The supportive elements can include the waistband and leg straps that are made of a material holding the knitted pouch, where the pouch can be formed of minimally supportive material to limit pressure on the genitalia. In this design the genitals are not held and supported over and against the pubic bone and a protective cup can be placed in the pouch.

Athletic supporters can be uncomfortable for the wearer. The straps attached to the backside of the supporter tend to move around and often have to be readjusted during activity. Furthermore, it is an inconvenience to have to put on and take off two separate articles of underwear for support, where underwear and the athletic supporter are worn together. These two waistbands (i.e., underwear waistband and supporter waistband) can together be overly tight and cause discomfort during activity. The waistbands can also shift independently during movement, thus decreasing the level of support and comfort that is needed and desired. One or both of the athletic supporter straps can also ride-up the backside of the wearer between the buttocks and can require frequent readjustment. There is nothing to stop the support straps from moving all around the buttocks and legs and further affect the position and tension of the pouch in the crotch region. With the exception of improvements in materials, the design of athletic supporters has changed minimally, although the need for support has increased due to changes in the type of physical and sporting activities that are prevalent, including additional medical uses for such garments.

Other supportive garments have focused on incorporating a protective cup within a sport brief. Such garments can be made of fabrics of various elasticities, such as a cotton/lycra combination. Because this design often contains one uniform fabric throughout, it may not offer enough durability or strength to hold and support the protective cup over and against the pubic bone to hold the genitals securely in place. The material can further permit the protective cup and/or genitals to move around and hence not provide adequate support or protection. Some materials (e.g., cotton/lycra fabric) may not provide enough elasticity or may not retain elasticity after being stretched during long workouts or heavy exertion, sweating, or repeated washings over the lifetime of the garment.

In some cases, compression shorts, made from nylon and lycra or spandex, can replace the typical athletic supporter in many non-contact sports and activities. Compression shorts can stretch as the person moves and can include wicking or moisture management fabrics to help the garment breathe and remove moisture. However, such garments may lack adequate support and protection for certain activities.

Accordingly, there is a need for improvement in supportive and protective garments.

SUMMARY

The present technology includes articles of manufacture, systems, and processes that relate to a garment having a integral support system, such as athletic briefs, shorts, swimwear, trunks, or various types of boxer/brief underwear. Objectives of the garment include providing an integrated support system for male genitalia. The garment can be in the form of briefs in sizes ranging from youth through adult. The garment can also be constructed and designed in the form of male briefs, trunks, and boxer briefs, providing active males, including both youth and adults, the choice of preference to their support system that is important for their comfort.

In some aspects, a garment for providing support to a wearer includes the following features. An article of clothing configured to cover at least the lower torso of the wearer. A pouch is disposed on a frontside of the article of clothing. Two straps are coupled to the pouch, where each strap is slidingly disposed through a separate channel formed in the article of clothing.

Additional aspects include where the article of clothing comprises a front portion and a back portion connected at a crotch portion, the front portion and the back portion defining a waist opening and the front portion, back portion, and crotch portion defining two leg openings. The waist opening can comprise an elastic waistband, drawcord, button, snap, clip, or hook-and-loop closure. The pouch can be coupled to the front portion proximate to the waist opening. The two straps can include a first strap having a first end and a second end and a second strap having a first end and a second end. The two channels can include a first channel formed in at least one of the crotch portion, the back portion, and the front portion and a second channel formed in at least one of the crotch portion, the back portion, and the front portion. The first end of the first strap and the first end of the second strap can be coupled to the pouch and the second end of the first strap and the second end of the second strap can be coupled to the back portion or the front portion, wherein a length of the first strap can be disposed in the first channel and a length of the second strap can be disposed in the second channel. The first strap can be configured to traverse a portion of one buttock of the wearer and the second strap can be configured to traverse a portion of the other buttock of the wearer. The first channel can be positioned on the back portion to traverse a portion of one buttock of the wearer and the second channel is positioned on the back portion to traverse a portion of the other buttock of the wearer. The first channel can comprise a width that limits lateral movement of the first strap and the second channel can comprise a width that limits lateral movement of the second strap. A spacing between the first strap and the second strap can increase in a direction from the crotch portion to the waist opening on the back portion. The waist opening can include a waistband where the pouch depends from the waistband. The first strap and the second strap can be configured to run to the back portion of the garment between the leg openings. The first strap and the second strap can be coupled to the back portion of the garment proximate to the waistband.

In various aspects, a garment for providing support to a wearer includes the following features. An article of clothing configured to cover at least the lower torso of the wearer. A pouch disposed on a frontside of the article of clothing. Two straps coupled to the pouch where each strap is slidingly disposed through a separate aperture formed in the article of clothing.

In certain aspects, a garment for providing support to a wearer includes the following features. An article of clothing configured to cover at least the lower torso of the wearer. A pouch disposed on a frontside of the article of clothing. Two straps coupled to the pouch and running to a backside of the article of clothing and coupled thereto, wherein each strap is slidingly disposed through a retaining means on the article of clothing.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
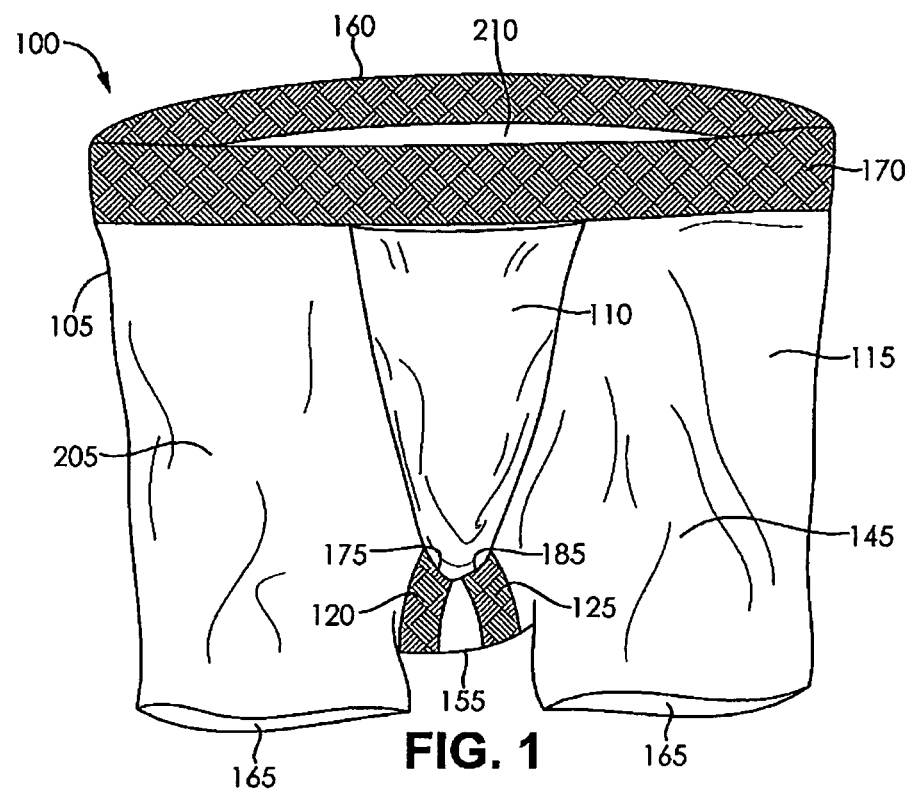
FIG. 1 illustrates a front view of a first embodiment of a garment according to the present disclosure.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding the methods disclosed, the order of the steps presented is exemplary in nature, and thus, the order of the steps can be different in various embodiments.

The present technology relates generally to an article of apparel, including a garment such as underwear, boxers, or briefs for a male wearer that has an integral support system. The integral support system, however, can be configured into any article of clothing that covers a portion of the lower torso of the wearer, including, by way of example and not by limitation, shorts, sweatpants, running shorts, bicycling shorts, swimwear, wetsuit, hospital gown, pajamas, military fatigues, etc. The garment with the integral support system can provide support and protection for male genitalia; i.e., the male scrotum, testes, and penis are referred to collectively as genitalia. The garment is configured to provide improved genital support while the wearer exercises, plays sports, or engages in a physical activity. This garment generally includes a portion configured as an article of clothing such as underwear, for example, made of cotton and spandex/elastane material, that contains a built-in support pouch, a wide waistband, support straps, and other supportive features. Various garment styles, including briefs, trunks, and boxer briefs can be used to suit wearer preferences. Additionally, the garment can be available in various sizes, including youth through adult sizes. Use of the garment can eliminate the need for the user to wear multiple support layers or uncomfortable compression underwear in order to gain adequate support while exercising, playing sports, or engaging in other physical activities.

In some embodiments, a garment for providing support to a wearer comprises an article of clothing, a pouch, and two straps. The article of clothing is configured to cover at least a portion of the lower torso of the wearer. The pouch is disposed on a frontside of the article of clothing. The two straps are coupled to the pouch and each strap is slidingly disposed through a separate channel formed in the article of clothing.

For example, the article of clothing can comprise a front portion and a back portion connected at a crotch portion. The front portion and the back portion can define a waist opening. The front portion, back portion, and crotch portion can define two leg openings. The front portion and the back portion can come together at the wearer's hips, for example. The pouch can be coupled at one or more points to the front portion and can be configured to accommodate the genitals of a male wearer. The first strap can include a first end and a second end. The second strap can include a first end and a second end. The first end of the first strap and the first end of the second strap can be coupled to the pouch. In some cases, the first end of the first strap and the first end of the second strap can both be coupled to the pouch via a single strap, where the single strap attaches to the pouch; e.g., forming a shape similar to the letter "Y." The second end of the first strap and the second end of the second strap can be coupled to the back portion or the front portion of the article of clothing. For example, the first end of the first strap and the first end of the second strap can be coupled to the pouch and traverse the crotch portion to the back portion where the second end of the first strap and the second end of the second strap are coupled to the back portion. In some cases, the first end of the first strap and the first end of the second strap can be coupled to the pouch and traverse the crotch portion to the back portion and wrap around the wearer's legs or hips where the second end of the first strap and the second end of the second strap are coupled to the front portion. A length of the first strap can be disposed in a first channel formed in the crotch portion, the back portion, and/or the front portion. A length of the second strap can be disposed in a second channel formed in the crotch portion, the back portion, and/or the front portion.

The garment can include various additional features. For example, one or more portions of the garment can comprise an absorbent material, a wicking material, or an elastic material. These materials can include natural and/or synthetic fibers, such as cotton, bamboo, hemp, silk, wool, rayon, polyester, cotton and polyester blends, elastane (spandex), rubber, nylon, nylon/polyester/elastane blends, polyethylene terephthalate, polypropylene, and other materials and combinations and blends thereof. Various weaves, knits, and warp knit constructions can be used, including tricot, raschels, milanese, powernets, ribs, meshes, lockstitches, etc. and various circular knit constructions can be used including single knits, double knits, ribs, jacquard, plaited, etc. The front portion of the article of clothing can include a flap or opening to aid the wearer when urinating so that the garment does not need to be removed. The waist opening can include an elastic waistband, drawcord, button, snap, clip, hook-and-loop closure, etc. and the flap can include these or other various closure means.

The pouch can be configured in several ways. The pouch can be configured to accommodate the genitalia of a male wearer. The pouch can be coupled to the front portion proximate to the waist opening and can be reversibly coupled to the article of clothing using hook-and-loop attachments, snaps, buttons, or other means. Other portions of the garment can be used for coupling the pouch and various portions of the pouch can be coupled to the garment. For example, the top of the pouch can be coupled proximate to the waist opening and/or the sides of the pouch can be coupled to the frontside of the garment. The pouch can comprise an elastic material and the elastic material can have different properties from a remainder of the garment. For example, the pouch can be more or less elastic than the remainder of the garment. The pouch can also be made of a material that is relatively inflexible and can be preformed to the shape of the wearer's genitalia. Varying degrees of rigidity can be employed for the pouch to impart varying degrees of support and protection. In certain cases, the pouch can take the form of a protective cup, a pocket for receiving a protective cup, or a pocket that includes a protective cup. The protective cup can include one or more reinforced fabrics, molded polymer articles including various thermoplastics, a para-aramid synthetic fiber such as Kevlar™, composites thereof, and combinations thereof. The pouch can comprise a moisture wicking material or layer and can the material can be perforated or ventilated in various ways.

Regarding the first and second straps, these straps can comprise an elastic material that can have elastic properties different from a remainder of the garment. In this way, the first strap and the second strap can stretch at a different rate than the remainder of the garment and can support the wearer's genitalia independent of stretch and movement of the rest of the garment. The straps can be of varying widths and thickness and can be formed of various materials. In some instances, the straps or the surface of the straps that may contact a portion of the article of clothing can be configured to have reduced friction with the remainder of the article of clothing in order to improve function and reduce wear. For example, nylon materials, particular weaves, coatings (e.g, Teflon™ finishes), and smooth finishes can allow the straps to slide easily against and through other portions of the garment. Reduced friction can ease sliding and/or stretching of the straps relative to a remainder of the garment.

There are various ways to configure the channels of the garment. The first channel can be positioned on the back portion of the garment to traverse a portion of one buttock of the wearer and the second channel can be positioned on the back portion of the garment to traverse a portion of the other buttock of the wearer. The first channel can have a width limiting lateral movement of the first strap and the second channel can have a width limiting lateral movement by the second strap. That is, the channel widths may be substantially similar to the strap widths, for example, so that the straps have little side-to-side movement within the channels. In this way, the straps are prevented from sliding laterally across the wearer's buttocks and are prevented from twisting or slipping between the wearer's buttocks.

The channels can be formed by placing the straps between two or more pieces of material and stitching or binding the pieces of material together to define the respective channel widths. In certain cases, the channels can be formed by disposing the straps on the article of clothing, placing a single piece of material over the straps, and stitching or binding the single piece of fabric on each side of the straps to form the channels. The channels can alternatively be formed using one or more separate pieces of material for each strap and stitching or binding the separate pieces of material on each side of the straps to form the channels.

The first and second channels can also comprise various lengths so that various lengths of the first and second straps are disposed within the channels. For example, the channels can run substantially from the crotch portion to the back portion of the garment and can even extend around the wearer's hips to the front portion of the garment. In some instances, the channels may traverse the back portion and end at the waist opening. In other instances, the channels may traverse the back portion and end at the waist opening on the front portion. Multiple channels and channels of various lengths can be employed for each strap, as well. In certain instances, the channels can be short where each of the channels can take the form of one or more bands for holding the straps. For example, the channel length can be less than the strap width. Longer channels, however, can better prevent the straps from twisting and can better control the spacing between the straps.

A spacing between the first strap and/or the first channel with respect to the second strap and/or the second channel can also increase in a direction from the crotch portion of the garment to the waist opening on the back portion and/or front portion of the garment. For example, the straps may touch or be close to each other at the crotch portion of the garment and then angle apart and each run across a buttock of the wearer until they are coupled at or near the waist opening at or near the wearer's hips.

The garment can be configured in different ways. For example, in some garments the pouch, the first strap, and the second strap are outside of the article of clothing. In other embodiments, the pouch, the first strap, and the second strap are inside of the article of clothing. The garment can also have a waist opening including a waistband, such as an elastic waistband, where the pouch depends or hangs down from the waistband. The first strap and the second strap can be configured to run to the back portion of the garment between the leg openings. The first strap and the second strap can also be coupled to the backside or the frontside of the article of clothing proximate to the waistband. In some cases, the second end of the first strap and the second end of the second strap can be coupled to the front portion, where the straps run from the back portion around the hips of the wearer to the front portion. The straps can therefore be coupled to the frontside of the article of clothing proximate to the waistband. The garment can take the form of various athletic garments, casual garments, or dress garments depending on the end use. Examples include underwear, boxers, briefs, shorts, sweatpants, running shorts, bicycling shorts, swimwear, wetsuit, hospital gown, pajamas, or military fatigues.

In various embodiments, a garment for providing support to a wearer comprises an article of clothing, a pouch, and two straps. The article of clothing is configured to cover at least a portion of the lower torso of the wearer. The pouch is disposed on a frontside of the article of clothing. The two straps are coupled to the pouch where each strap is slidingly disposed through a separate aperture formed in the article of clothing.

Such garments can also include one or more of the various other features as described herein.

The apertures in the article of clothing can function in a manner similar to the channels discussed herein. For example, one aperture can be positioned on the backside over one buttock of the wearer and the other aperture can be positioned on the backside over the other buttock of the wearer. The apertures can each have a width limiting lateral movement of the strap passing therethrough. That is, the aperture widths may be substantially similar to the strap widths, for example, so that the straps have little side-to-side movement within the apertures. In this way, the straps are prevented from sliding laterally across the wearer's buttocks and are prevented from twisting or slipping between the wearer's buttocks. The apertures can also take the form of various sizes and shapes, such as slots or slits in the article of clothing. The edges of the apertures can include binding or reinforcement to improve durability and abrasion resistance as the straps slide and/or stretch through the apertures.

Such garments can also be configured so that the pouch is outside of the article of clothing so that the straps coupled to the pouch run to the backside of the article of clothing and pass through the apertures to the inside of the article clothing. Conversely, in other configurations the pouch can be inside of the article of clothing and the straps coupled to the pouch run to the backside of the article of clothing and pass through the apertures to the outside of the article of clothing. There can also be multiple apertures for each strap so that the straps pass through from the outside/inside to the inside/outside and back to the outside/inside one or more times. Thus, the straps can weave through the article of clothing one or more times. Spacing of the apertures for each strap can vary to change the aperture spacing as the straps weave therethrough and/or to change the spacing between the different straps as the straps traverse the article of clothing. In some cases, the straps run from the pouch and are coupled to the backside of the article of clothing proximate to the waistband. In other cases, the straps run from the pouch to the back portion and around the hips of the wearer to the front portion where the straps are coupled to the frontside of the article of clothing proximate to the waistband.

In certain embodiments, a garment for providing support to a wearer includes an article of clothing configured to cover at least the lower torso of the wearer. A pouch is disposed on a frontside of the article of clothing. Two straps are coupled to the pouch, each strap slidingly disposed through a retaining means formed in the article of clothing. Each retaining means can comprise a channel or an aperture as described. Other retaining means can be used to space and retain the straps on the article of clothing with the caveat that the straps are allowed to slide relative to the retaining means. Further examples of such retaining means include troughs, clips, hooks, rings, and the like formed in or disposed on the article of clothing.

The present technology provides several benefits. One benefit includes maintaining the spacing of the straps across the article of clothing thereby limiting lateral movement of the straps. The straps are therefore kept from laterally sliding around and from sliding between the buttocks of the wearer. Another benefit is that the straps are kept from twisting due to the limited lateral movement of the straps. This improves comfort as twisted straps can have altered elastic behavior, can affect position of the pouch, and can form pressure points. Yet another benefit is the ability of the straps to independently move and slide relative to the remainder of the garment. For example, where the straps are elastic in character, the straps can stretch differently than the remainder of the garment. Thus, the pouch can retain support and protection independent of the stretch, position, and movement of the other portions of the garment as the wearer moves or exercises.

EXAMPLES

Figure 2:
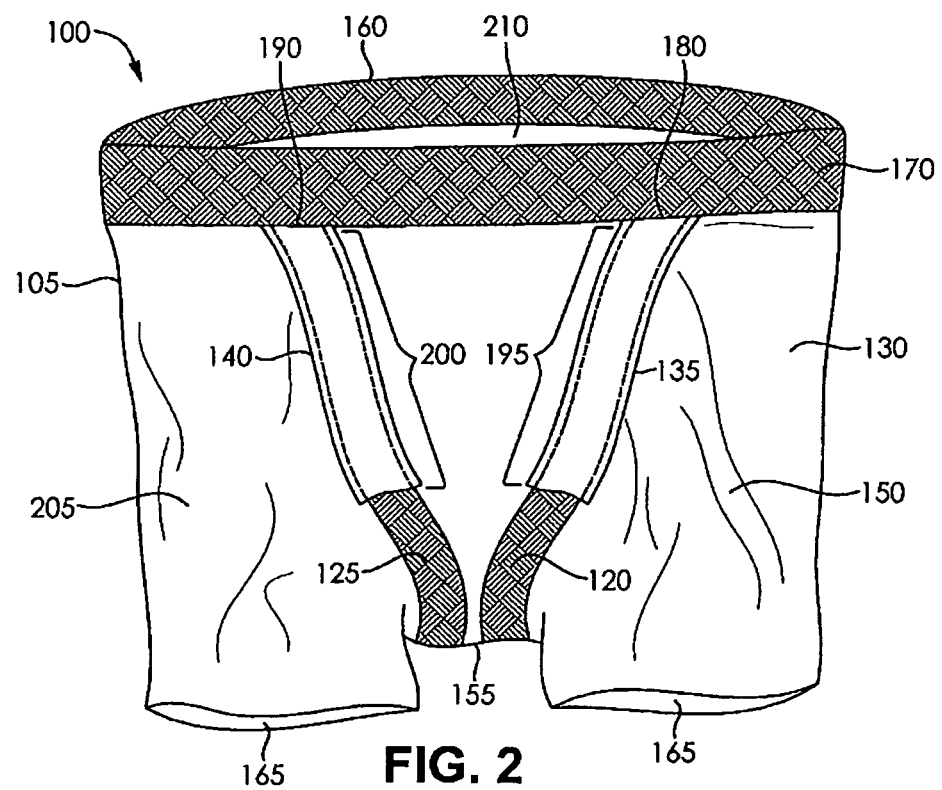
FIG. 2 illustrates a back view of the first embodiment of a garment according to the present disclosure.

With reference to FIGS. 1 and 2, a first embodiment of a garment 100 for providing support to a wearer is shown. The garment 100 includes an article of clothing 105 configured to cover at least the lower torso of the wearer, where a boxer-brief style is shown. A pouch 110 is disposed on a frontside 115 of the article of clothing 105. Two elastic straps 120, 125 are coupled to the pouch 110 and run to a backside 130 of the article of clothing 105 and are coupled thereto. Each strap 120, 125 is slidingly disposed through a separate channel 135, 140 formed in the backside 130 of the article of clothing 105.

As shown, the article of clothing 105 includes a front portion 145, a back portion 150, and a crotch portion 155. The front portion 145 and the back portion 150 define a waist opening 160 and the front portion 145, back portion 150, and crotch portion 155 define two leg openings 165. The waist opening 160 includes an elastic waistband 170. The pouch 110 is coupled to the front portion 145 proximate to the waist opening 160 and waistband 170. The two straps 120, 125 include a first strap 120 having a first end 175 and a second end 180 and a second strap 125 having a first end 185 and a second end 190. The two channels 135, 140 include a first channel 135 formed in the back portion 150 and a second channel 140 formed in the back portion 150. The first end 175 of the first strap 120 and the first end 185 of the second strap 125 are coupled to the pouch 110 and the second end 180 of the first strap 120 and the second end 190 of the second strap 125 are coupled to the back portion 150. As shown, the second ends 180, 190 are coupled proximate to the waistband 170. A length 195 of the first strap 120 is disposed in the first channel 135 and a length 200 of the second strap 125 is disposed in the second channel 140.

As shown, the first strap 120 is configured to traverse a portion of one buttock of the wearer and the second strap 125 is configured to traverse a portion of the other buttock of the wearer. Likewise, the first channel 135 is positioned on the back portion 150 to traverse a portion of one buttock of the wearer and the second channel 140 is positioned on the back portion 150 to traverse a portion of the other buttock of the wearer. The first channel 135 comprises a width that limits lateral movement of the first strap 120 and the second channel 140 comprises a width that limits lateral movement of the second strap 125, where the channel widths are slightly larger than the strap widths. Spacing between the first strap 120 and the second strap 125 increases in a direction from the crotch portion 155 to the waist opening 160 on the back portion 150.

The pouch 110 is shown depending from the waistband 170 and the first strap 120 and the second strap 125 are configured to run to the back portion 150 of the garment between the leg openings 165. The first strap 120 and the second strap 125 are coupled to the back portion 150 of the garment 100 proximate to the waistband 170. As depicted in FIGS. 1 and 2, the pouch 110 and the two straps 120, 125 are outside 205 of the article of clothing 105. However, the garment 100 can be configured so that the pouch 110 and the two straps 120, 125 are inside 210 of the article of clothing 105. In this way, the straps 120, 125 are slidingly disposed through separate channels 135, 140 on the inside 210 of the backside 130 of the article of clothing (not shown).

Figure 3:
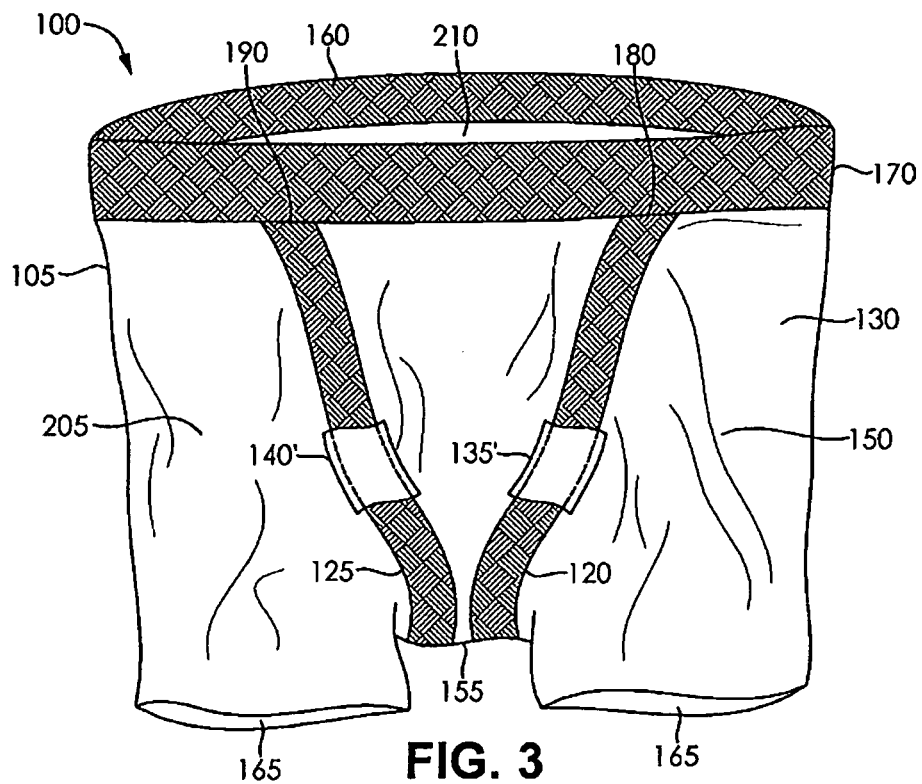
FIG. 3 illustrates a back view of a second embodiment of a garment according to the present disclosure.

As depicted in FIG. 3, a second embodiment of the backside 130 of the garment 100 is shown. Here, the channels 135', 140' are shorter than the channels 135, 140 shown in FIG. 2.

The frontside 115 of the garment 100 is the same as shown for the first embodiment in FIG. 1.

Figure 4:
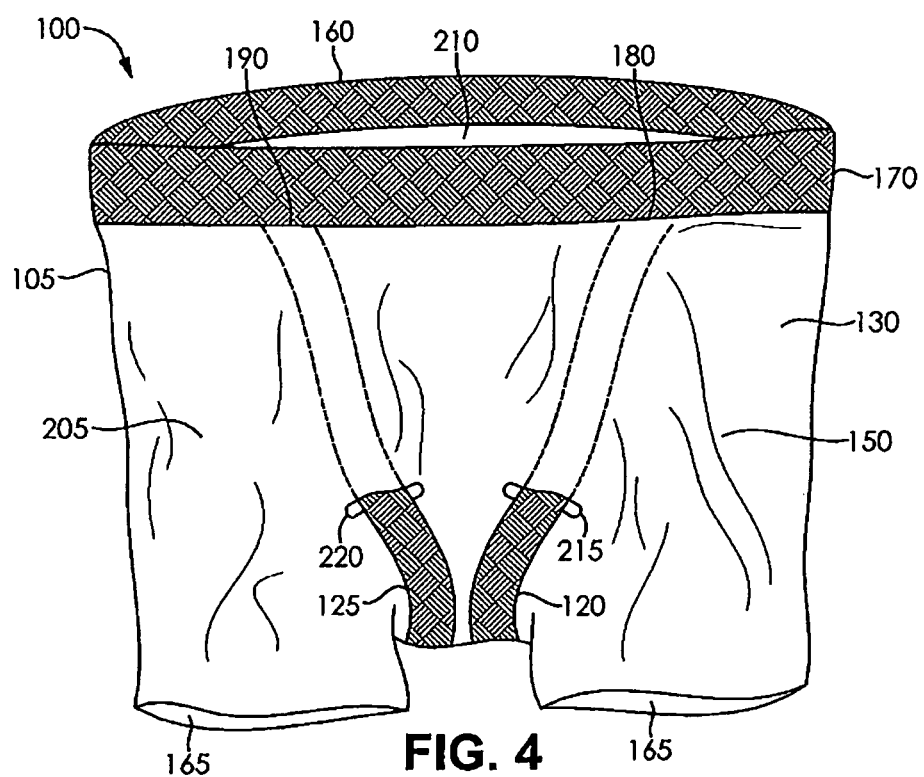
FIG. 4 illustrates a back view of a third embodiment of a garment according to the present disclosure.

With reference to FIG. 4, a third embodiment of the backside 130 of the garment 100 is shown. In the third embodiment, the garment 100 for providing support to a wearer includes two straps 120, 125 coupled to the pouch 110 and running to the backside 130 of the article of clothing 105 and coupled thereto. Each strap 120, 125 is slidingly disposed through a separate aperture 215, 220 formed in the backside 130 of the article of clothing 105. As shown, the pouch 110 is outside 205 of the article of clothing 105 and the straps 120, 125 coupled to the pouch 110 run to the backside 130 of the article of clothing 105 and pass through the apertures 215, 220 to the inside 210 of the article of clothing 105. However, the garment 100 can be configured so that the pouch 110 is inside 210 of the article of clothing 105 and the straps 120, 125 coupled to the pouch 110 run to the backside 130 of the article of clothing 105 and pass through the apertures 215, 220 to the outside 205 of the article of clothing (not shown). The frontside 115 of the garment 100 is the same as shown for the first embodiment in FIG. 1.

Figure 5:
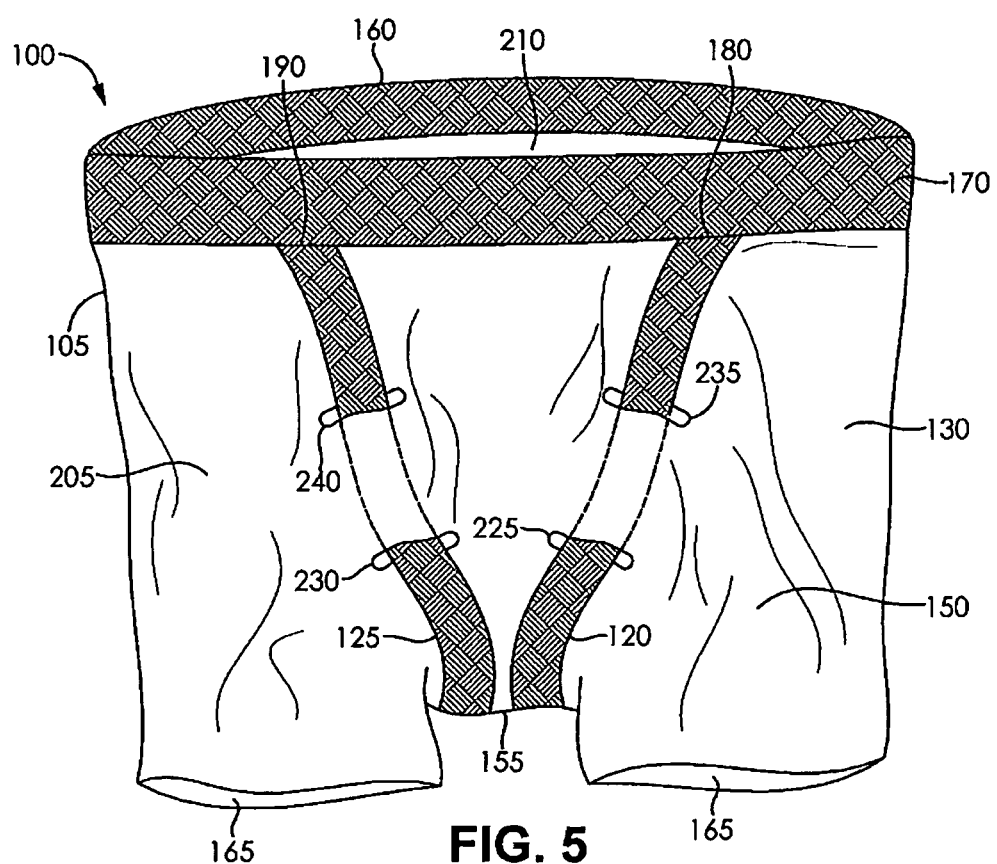
FIG. 5 illustrates a back view of a fourth embodiment of a garment according to the present disclosure.

Shown in FIG. 5 is a fourth embodiment of the backside 130 of the garment 100. Here, the straps 120, 125 are coupled to the pouch 110 and pass from the outside 205 through first apertures 225, 230 to the inside 210 of the article of clothing 105 and then pass through second apertures 235, 240 back to the outside 205 of the article of clothing 105. The frontside 115 of the garment 100 is the same as shown for the first embodiment in FIG. 1.

Figure 6:
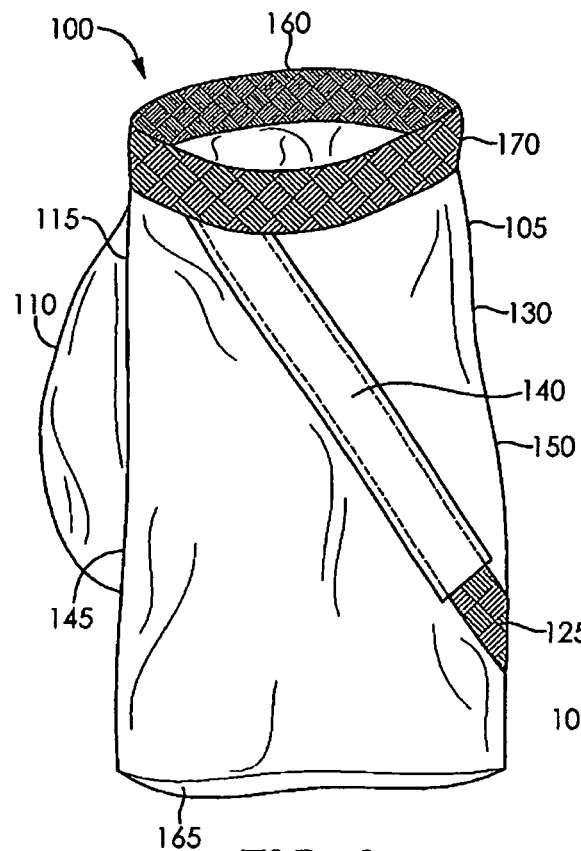
FIG. 6 illustrates a left side view of a fifth embodiment of a garment according to the present disclosure.

FIG. 6 illustrates left side view of a fifth embodiment of the garment 100. The fifth embodiment is similar to the first embodiment shown in FIGS. 1 and 2, except that the first strap 120 and the second strap 125 are coupled to the front portion 145 on the frontside 115 of the article of clothing 105, where the first strap 120 and the second strap 125 run from the back portion 150 on the backside 130 of the article of clothing around the hips of the wearer to the front portion 145. Likewise, the first channel 135 and the second channel 140 run from the back portion 150 to the front portion 145. The right side (not shown) of the garment 100 is generally symmetrical to the left side.

Figure 7:
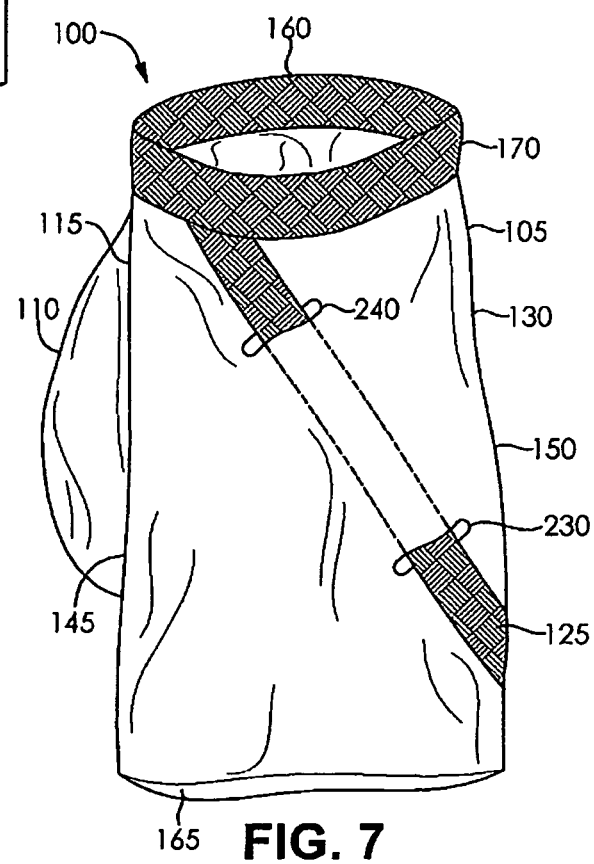
FIG. 7 illustrates a left side view of a sixth embodiment of a garment according to the present disclosure.

With respect to FIG. 7, a left side view of a sixth embodiment of the garment 100 is shown. The sixth embodiment is similar to the fourth embodiment shown in FIG. 5, except that the first strap 120 and the second strap 125 are coupled to the front portion 145 on the frontside 115 of the article of clothing 105, where the first strap 120 and the second strap 125 run from the back portion 150 on the backside 130 of the article of clothing around the hips of the wearer to the front portion 145. The straps 120, 125 pass through first apertures 225, 230 on the back portion 150 and pass through second apertures 235, 240 on the front portion 145. The right side (not shown) of the garment 100 is generally symmetrical to the left side.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A garment for providing support to a wearer comprising:
an article of clothing configured to cover at least a portion of the lower torso of the wearer, the article of clothing including a front portion and a back portion connected at a crotch portion, the front portion and the back portion defining a waist opening and the front portion, back portion, and crotch portion defining two leg openings;
a pouch disposed on a frontside of the article of clothing; and two straps coupled to the pouch, each strap slidingly disposed through a separate channel formed in the article of clothing, the two straps including a first strap having a first end and a second end and a second strap having a first end and a second end, the two channels including a first channel formed in at least one of the crotch portion, the back portion, and the front portion, and a second channel formed in at least one of the crotch portion, the back portion, and the front portion, the first end of the first strap and the first end of the second strap coupled to the pouch and the second end of the first strap and the second end of the second strap coupled to at least one of the front portion and the back portion, a length of the first strap disposed in the first channel, a length of the second strap disposed in the second channel, the waist opening including a waistband, the pouch directly depending from the waistband, the first strap and the second strap configured to extend to the back portion of the garment between the leg openings, and the first strap and the second strap coupled to the garment proximate to the waistband.

2. The garment of claim 1, wherein the pouch is configured to accommodate the genitalia of a male wearer.

3. The garment of claim 1, wherein the pouch comprises a protective cup, a pocket for receiving a protective cup, or a pocket including a protective cup.

4. The garment of claim 1, wherein the two straps comprise an elastic material.

5. The garment of claim 1, wherein the waist opening comprises an elastic waistband, drawcord, button, snap, clip, or hook-and-loop closure.

6. The garment of claim 1, wherein the pouch is coupled to the front portion proximate to the waist opening.

7. The garment of claim 1, wherein the first strap is configured to traverse a portion of one buttock of the wearer and the second strap is configured to traverse a portion of the other buttock of the wearer.

8. The garment of claim 1, wherein the first channel is positioned on the back portion to traverse a portion of one buttock of the wearer and the second channel is positioned on the back portion to traverse a portion of the other buttock of the wearer.

9. The garment of claim 1, wherein the first channel comprises a width that limits lateral movement of the first strap and the second channel comprises a width that limits lateral movement of the second strap.

10. The garment of claim 1, wherein a spacing between the first strap and the second strap increases in a direction from the crotch portion to the waist opening on the back portion.

11. The garment of claim 1, wherein the pouch and the two straps are outside of the article of clothing.

12. The garment of claim 1, wherein the pouch and the two straps are inside of the article of clothing.

13. A garment for providing support to a wearer comprising:
- an article of clothing configured to cover at least a portion of the lower torso of the wearer, the article of clothing including a front portion and a back portion connected at a crotch portion, the front portion and the back portion defining a waist opening and the front portion, back portion, and crotch portion defining two leg openings;
- a pouch disposed on a frontside of the article of clothing; and two straps coupled to the pouch, each strap slidingly disposed through a separate aperture formed in the article of clothing, the two straps including a first strap having a first end and a second end and a second strap having a first end and a second end, the two apertures including a first aperture formed in at least one of the crotch portion, the back portion, and the front portion, and a second aperture formed in at least one of the crotch portion, the back portion, and the front portion, the first end of the first strap and the first end of the second strap coupled to the pouch and the second end of the first strap and the second end of the second strap coupled to at least one of the front portion and the back portion, a length of the first strap disposed through the first aperture, a length of the second strap disposed through the second aperture, the waist opening including a waistband, the pouch directly depending from the waistband, the first strap and the second strap configured to extend to the back portion of the garment between the leg openings, and the first strap and the second strap, coupled to the garment proximate to the waistband.

14. The garment of claim 13, wherein the pouch is outside of the article of clothing and the straps coupled to the pouch pass through the apertures to the inside of the article of clothing.

15. The garment of claim 13, wherein the pouch is inside of the article of clothing and the straps coupled to the pouch pass through the apertures to the outside of the article of clothing.

16. A garment for providing support to a wearer comprising:
- an article of clothing configured to cover at least a portion of the lower torso of the wearer, the article of clothing including a front portion and a back portion connected at a crotch portion, the front portion and the back portion defining a waist opening and the front portion, back portion and crotch portion defining two leg openings;
- a pouch disposed on a frontside of the article of cloning; and
- two straps coupled to the pouch, each strap slidingly disposed through a retaining means formed in the article of clothing, the two straps including a first strap having a first end and a second end and a second strap having a first end and a second end, the two retaining means including a first retaining means formed in at least one of the crotch portion, the back portion, and the front portion, and a second retaining means formed in at least one of the crotch portion, the back portion, and the front portion, the first end of the first strap and the first end of the second strap coupled to the pouch and the second end of the first strap and the second end of the second strap coupled to at least one of the front portion and the back portion, a length of the first strap retained by the first retaining means, a length of the second strap retained by the second retaining means, the waist opening including a waistband, the pouch directly depending from the waistband, the first strap and the second strap configured to extend to the back portion of the garment between the leg openings, and the first strap and the second strap coupled to the garment proximate to the waistband.

17. The garment of claim 1, wherein the first end of the first strap and the first end of the second strap are coupled to a lower portion of the pouch away from the waist opening.

* * * * *